US009808211B2

(12) United States Patent
Yorkston et al.

(10) Patent No.: US 9,808,211 B2
(45) Date of Patent: Nov. 7, 2017

(54) HEAD AND NECK IMAGER

(71) Applicant: Carestream Health, Inc., Rochester, NY (US)

(72) Inventors: John Yorkston, Penfield, NY (US); William C. Wendlandt, Rush, NY (US); Peter A. Newman, Pittsford, NY (US); Donna K. Rankin-Parobek, Honeoye Falls, NY (US); David Y. Chan, Mississauga (CA)

(73) Assignee: Carestream Health, Inc., Rochester, NY (US)

( * ) Notice: Subject to any disclaimer, the term of this patent is extended or adjusted under 35 U.S.C. 154(b) by 263 days.

(21) Appl. No.: 14/537,085

(22) Filed: Nov. 10, 2014

(65) Prior Publication Data

US 2015/0131775 A1 May 14, 2015

Related U.S. Application Data

(60) Provisional application No. 61/902,819, filed on Nov. 12, 2013.

(51) Int. Cl.
*A61B 6/03* (2006.01)
*A61B 6/00* (2006.01)
(Continued)

(52) U.S. Cl.
CPC .............. *A61B 6/035* (2013.01); *A61B 6/025* (2013.01); *A61B 6/032* (2013.01); *A61B 6/4007* (2013.01);
(Continued)

(58) Field of Classification Search
CPC ........... A61B 6/025; A61B 6/03; A61B 6/032; A61B 6/035; A61B 6/4007; A61B 6/4085;
(Continued)

(56) References Cited

U.S. PATENT DOCUMENTS 3,500,045 A     3/1970   Rossi
4,115,696 A *   9/1978   Truscott ................. A61B 6/032
                                                          378/13
(Continued)

FOREIGN PATENT DOCUMENTS

DE    10 2005 004 502 A1    8/2006
DE    10 2005 004502 A1    8/2006
(Continued)

OTHER PUBLICATIONS

International Search Report dated May 6, 2015 for International Application No. PCT/US2014/064905, 3 pages.

*Primary Examiner* — Allen C. Ho

(57) ABSTRACT

A CBCT imaging system comprises a digital radiation detector and radiation source. A detector transport moves the detector along at least a portion of a first curved path and a radiation source transport moves the radiation source along at least a portion of a second curved source path. The detector is configured to travel at least a portion of the first curved path, and the radiation source is configured to travel at least a portion of the second curved path. The detector is configured to obtain a plurality of 2D projection images over a range of scan angles for reconstructing a 3D volume image using the plurality 2D projection images.

19 Claims, 11 Drawing Sheets

(51) Int. Cl.
*A61B 6/02* (2006.01)
*A61B 6/04* (2006.01)
(52) U.S. Cl.
CPC .......... *A61B 6/4405* (2013.01); *A61B 6/4435* (2013.01); *A61B 6/4447* (2013.01); *A61B 6/4452* (2013.01); *A61B 6/501* (2013.01); *A61B 6/0442* (2013.01); *A61B 6/0457* (2013.01); *A61B 6/4085* (2013.01); *A61B 6/4266* (2013.01); *A61B 6/4275* (2013.01); *A61B 6/4482* (2013.01)
(58) Field of Classification Search
CPC ... A61B 6/4405; A61B 6/4435; A61B 6/4447; A61B 6/4452; A61B 6/501
USPC .................. 378/9, 10, 15, 17, 22, 27, 38–40, 378/196–198
See application file for complete search history.

(56) References Cited

U.S. PATENT DOCUMENTS

| | | | |
|---|---|---|---|
| 5,666,392 A | 9/1997 | Ploetz | |
| 5,872,828 A * | 2/1999 | Niklason | A61B 6/025 378/23 |
| 6,092,928 A * | 7/2000 | Mattson | A61B 6/08 378/197 |
| 6,200,024 B1 * | 3/2001 | Negrelli | A61B 6/4233 378/196 |
| 6,222,906 B1 * | 4/2001 | Sakaguchi | A61B 6/06 257/E27.132 |
| 6,236,708 B1 * | 5/2001 | Lin | A61B 6/025 378/22 |
| 6,325,537 B1 * | 12/2001 | Watanabe | A61B 6/4233 378/196 |
| 6,400,791 B1 * | 6/2002 | Schwarz | A61B 6/0457 378/15 |
| 6,435,715 B1 * | 8/2002 | Betz | A61B 6/4458 378/197 |
| 6,461,040 B1 * | 10/2002 | Mattson | A61B 6/08 378/205 |
| 6,496,558 B2 * | 12/2002 | Graumann | A61B 6/0478 378/197 |
| 6,580,777 B1 * | 6/2003 | Ueki | A61B 6/032 378/15 |
| 6,637,056 B1 * | 10/2003 | Tybinkowski | A61B 6/0457 378/209 |
| 6,683,935 B2 * | 1/2004 | Moore | A61B 6/035 378/17 |
| 6,814,489 B2 * | 11/2004 | Jensen | A61B 6/08 378/197 |
| 6,819,736 B1 * | 11/2004 | Bruder | A61B 6/032 378/15 |
| 6,831,961 B1 * | 12/2004 | Tybinkowski | A61B 6/032 250/363.04 |
| 6,882,700 B2 * | 4/2005 | Wang | A61B 6/502 378/197 |
| 6,999,554 B2 * | 2/2006 | Mertelmeier | A61B 6/0414 378/196 |
| 7,003,070 B1 * | 2/2006 | Chen | A61B 6/00 378/17 |
| 7,016,457 B1 * | 3/2006 | Senzig | A61B 6/032 378/116 |
| 7,020,236 B2 * | 3/2006 | Shechter | A61B 6/0457 378/15 |
| 7,108,421 B2 * | 9/2006 | Gregerson | A61B 6/032 378/146 |
| 7,212,606 B2 * | 5/2007 | Souchay | A61B 6/032 378/21 |
| 7,300,204 B2 * | 11/2007 | Gotoh | A61B 6/4441 378/197 |
| 7,338,207 B2 * | 3/2008 | Gregerson | A61B 6/032 378/17 |
| 7,379,526 B2 * | 5/2008 | Nishide | A61B 6/032 378/15 |
| 7,418,074 B2 * | 8/2008 | Du | A61B 6/032 378/13 |
| 7,453,979 B2 * | 11/2008 | Sendai | A61B 6/025 378/23 |
| 7,515,677 B2 * | 4/2009 | Zellerhoff | A61B 6/4441 378/196 |
| 7,515,679 B2 * | 4/2009 | Tacconi | A61B 6/032 378/15 |
| 7,591,587 B2 * | 9/2009 | Gotoh | A61B 6/4441 378/189 |
| 7,623,905 B2 * | 11/2009 | Haras | A61B 6/02 378/11 |
| 7,697,661 B2 * | 4/2010 | Souchay | A61B 6/025 378/21 |
| 7,778,388 B2 * | 8/2010 | Sendai | A61B 6/025 378/22 |
| 7,806,589 B2 * | 10/2010 | Tashman | A61B 5/1038 378/193 |
| 7,835,490 B2 * | 11/2010 | Ramsauer | A61B 6/0414 378/197 |
| 7,837,385 B2 * | 11/2010 | Klingenbeck-Regn | A61B 6/102 378/197 |
| 7,885,379 B2 * | 2/2011 | Meer | A61B 6/502 378/37 |
| 7,988,357 B2 * | 8/2011 | Hornung | A61B 6/4233 378/197 |
| 8,005,186 B2 * | 8/2011 | Lee | A61B 6/032 378/13 |
| 8,031,834 B2 * | 10/2011 | Ludwig | A61B 6/502 378/37 |
| 8,300,762 B2 * | 10/2012 | Suzuki | A61B 6/032 378/15 |
| 8,320,517 B2 * | 11/2012 | Dennerlein | A61B 6/032 378/4 |
| 8,363,050 B2 * | 1/2013 | Ludwig | A61B 6/025 345/419 |
| 8,475,040 B2 * | 7/2013 | Sanchez Calvo | A61B 6/025 378/196 |
| 8,553,837 B2 * | 10/2013 | Johansson | A61B 6/025 378/22 |
| 8,571,172 B2 * | 10/2013 | Dafni | A61B 6/032 378/11 |
| 8,662,749 B2 * | 3/2014 | Kia | G01N 23/04 378/189 |
| 8,693,621 B2 * | 4/2014 | Thran | A61B 6/4447 378/17 |
| 8,903,039 B2 * | 12/2014 | Masumoto | A61B 6/025 378/21 |
| 8,913,713 B2 * | 12/2014 | Masumoto | A61B 6/025 378/21 |
| 9,144,406 B2 * | 9/2015 | Dennerlein | A61B 6/025 |
| 9,282,942 B2 * | 3/2016 | Mertelmeier | A61B 6/502 |
| 9,298,194 B2 * | 3/2016 | Lee | A61B 6/4441 |
| 9,675,277 B2 * | 6/2017 | Arai | A61B 6/502 |
| 9,717,467 B2 * | 8/2017 | Litzenberger | A61B 6/032 |
| 2008/0310584 A1 | 12/2008 | Hey et al. | |
| 2010/0008474 A1 | 1/2010 | Hornung et al. | |

FOREIGN PATENT DOCUMENTS

| | | |
|---|---|---|
| EP | 2 599 439 A1 | 6/2013 |
| WO | 2008/035828 A1 | 3/2008 |

* cited by examiner

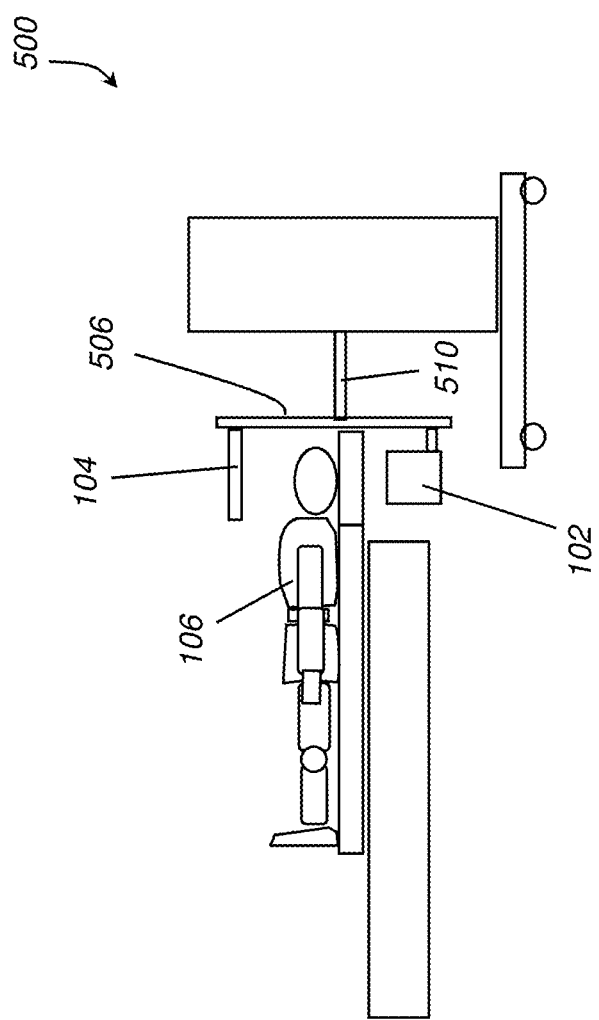

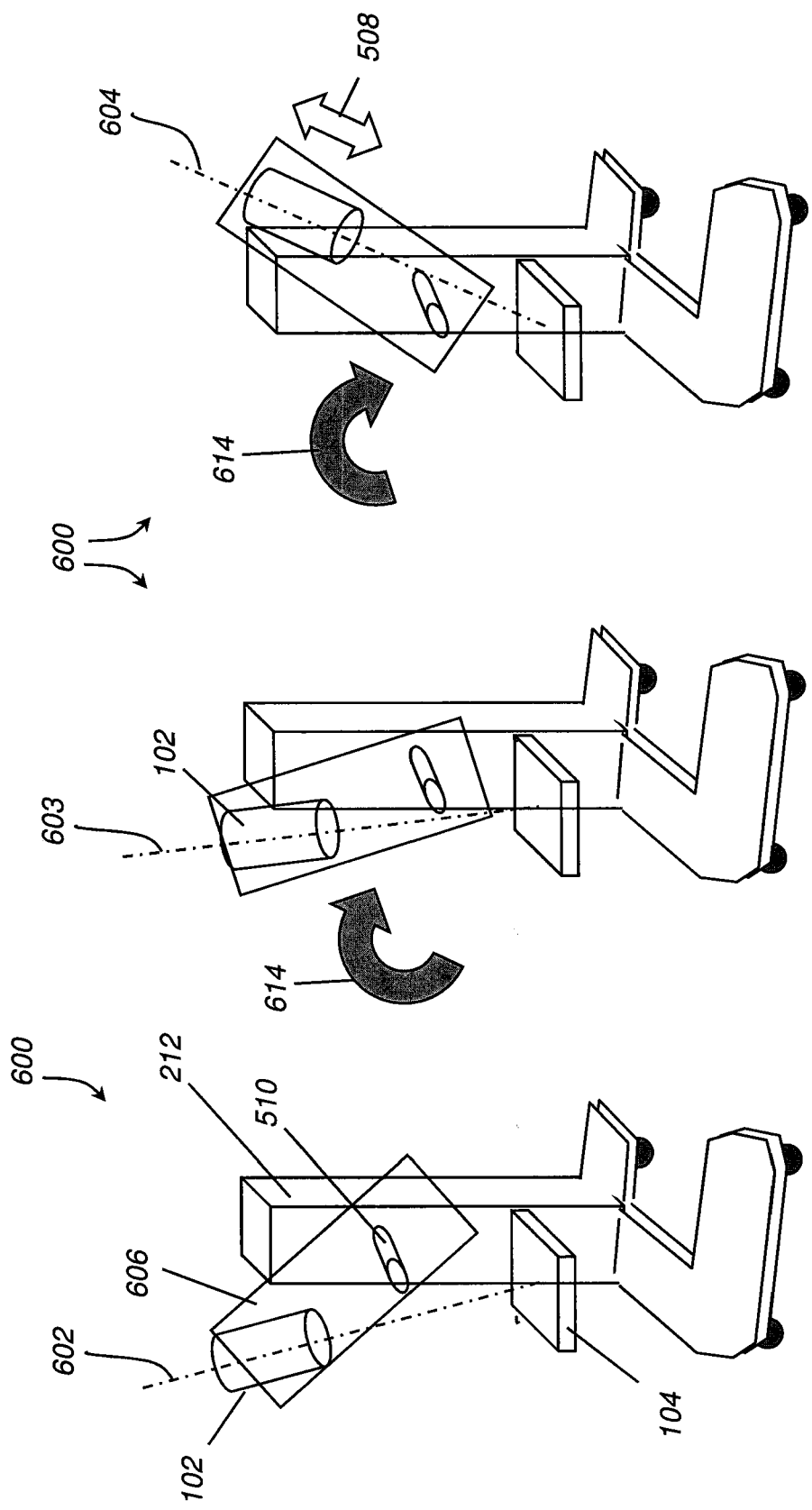

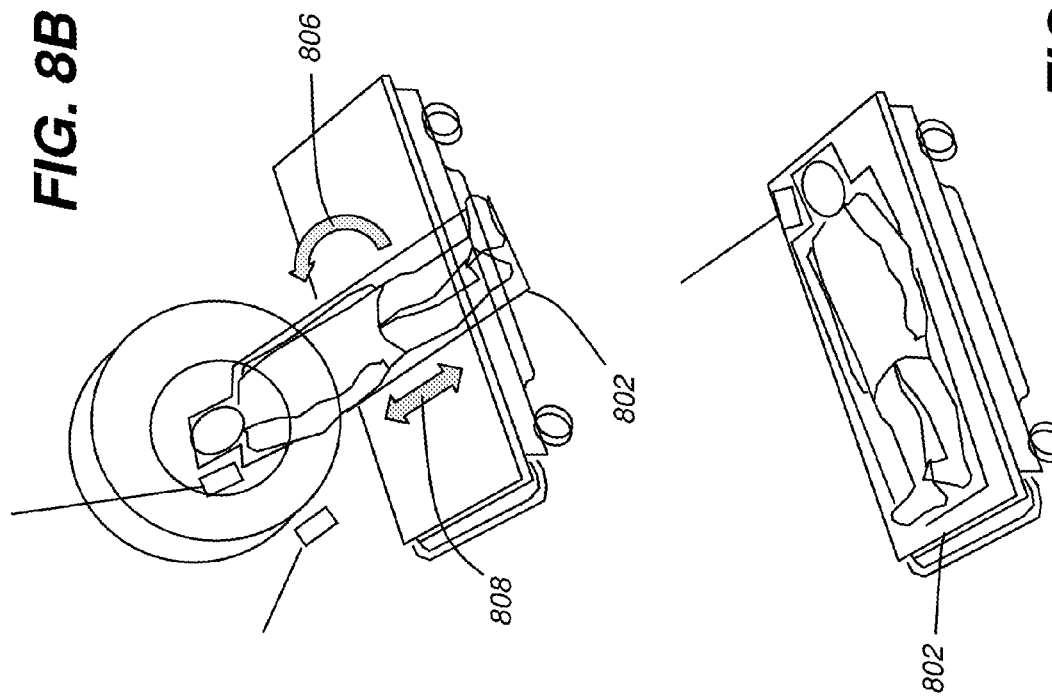
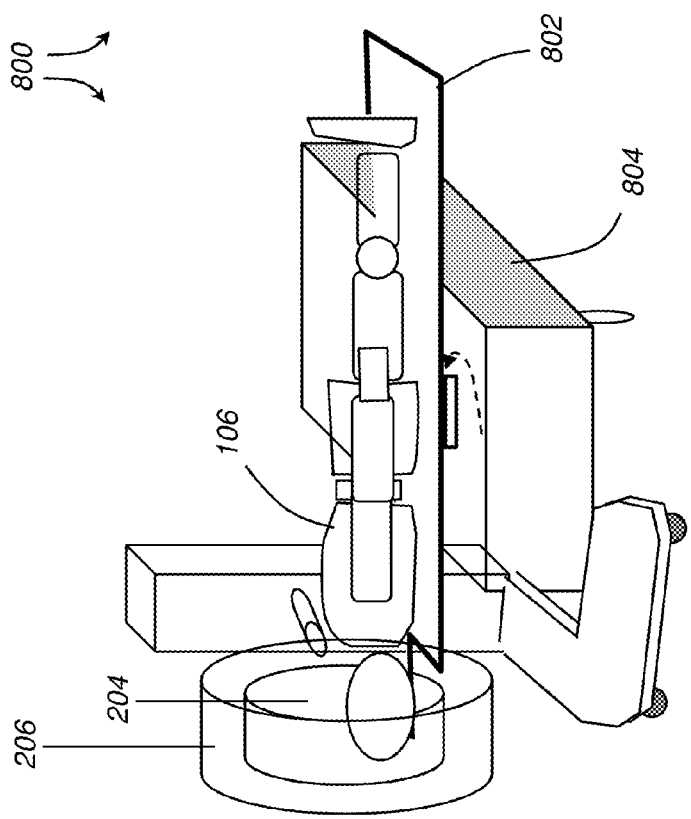
FIG. 8B
FIG. 8C
FIG. 8A

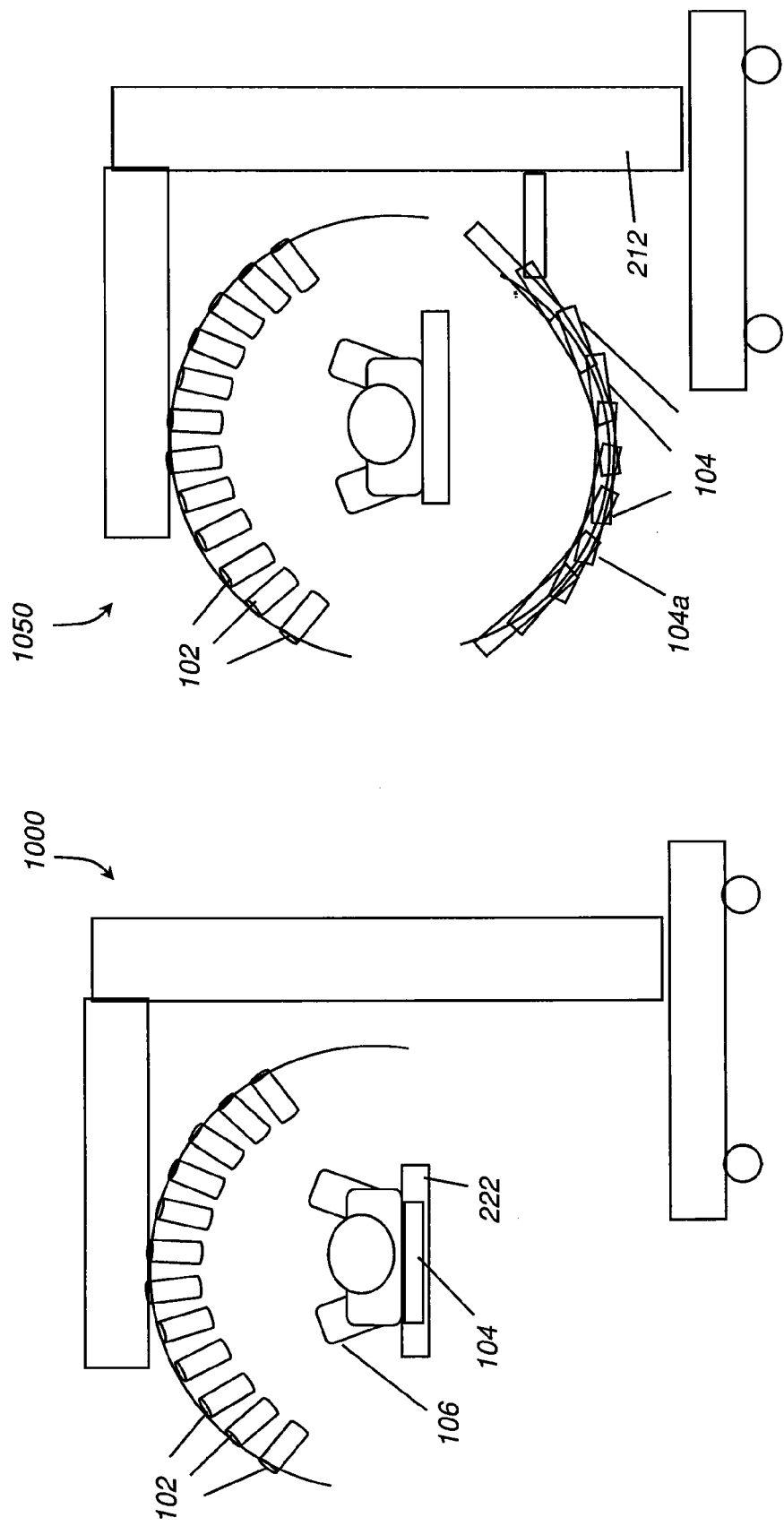

HEAD AND NECK IMAGER

CROSS REFERENCE TO RELATED APPLICATIONS

This application claims priority to U.S. Patent Application Ser. No. 61/902,819, filed Nov. 12, 2013, in the name of Yorkston et al., and entitled EXTREMITY IMAGING SCANNER FOR THE HEAD AND NECK.

This application is related in certain respects to U.S. Pat. No. 8,210,745, issued Jul. 3, 2012, in the name of Yorkston et al., and entitled EXTREMITY IMAGING APPARATUS FOR CONE BEAM COMPUTED TOMOGRAPHY; U.S. Pat. No. 8,348,506, issued Jan. 8, 2013, in the name of Yorkston et al., and entitled EXTREMITY IMAGING APPARATUS FOR CONE BEAM COMPUTED TOMOGRAPHY; U.S. Pat. No. 8,672,543, issued Mar. 18, 2014, in the name of Kralles et al., and entitled COUNTERWEIGHT FOR MOBILE X-RAY DEVICE; and U.S. Pat. No. 8,876,379, issued Nov. 4, 2014, in the name of DiRisio et al., and entitled COLLAPSIBLE COLUMN MOVEMENT APPARATUS FOR MOBILE X-RAY DEVICE; all of which are incorporated herein by reference in their entirety.

BACKGROUND OF THE INVENTION

The subject matter disclosed herein relates to Cone Beam Computed Tomography (CBCT) imaging, in particular, to systems and methods related to a head and neck scanner using CBCT imaging.

Cone-Beam Computed Tomography (CBCT) imaging and other related 3D volume imaging modes including tomosynthesis have significant value as diagnostic and clinical tools for evaluation of injury or illness related to the head and neck. However, workable systems have not been available for CBCT imaging in intensive care unit (ICU) or emergency room (ER) environments. Instead, patients for whom this type of imaging is useful must be transported from the ICU, ER, or other facility to the radiographic imaging site. There may be an element of risk and time loss due to the need for transporting the patient. Transport may be particularly difficult in cases of spinal injury, for example. The imaging task may be further complicated where the patient may be connected to life support systems, tubing, monitors, and other equipment common to ICU and ER facilities.

There would be benefits to a portable system that provides CBCT and other volume imaging of the head and neck, with imaging of the full set of cervical vertebrae (C1-C7) and at least as far as the top thoracic vertebra T1. The portable apparatus should be usable in ICU and ER environments, as well as for sports medicine, ENT (ear-nose-throat), and other diagnostic situations requiring head and neck imaging.

With reference to FIG. 1A, radiographic images may be obtained in operation of CBCT imaging system 100 by directing radiation 103 through the patient 106 at successive angular positions, e.g., revolving a radiation source 102 clockwise from a start position 110 to an end position 111, and capturing an image at each angular position. The image acquisition system includes at least one radiation source 102, at least one detector 104, and related components that support orbiting, or revolving, the radiation source 102 and the detector 104 over the range of angles 110-111 as needed for the imaging mode. For CBCT imaging, the radiation source 102 and detector 104 are substantially 180 degrees apart throughout the orbit, with the patient 106 between them at every imaging position. FIG. 1A shows a top view of radiation source 102 and detector 104 movement in a CBCT imaging apparatus 100 for a patient 106 who is standing and is able to maintain a vertical head position. The radiation source 102 may be capable of revolving around the circular source orbit 108.

FIG. 1B shows one of the difficulties of head and neck imaging where a patient 106 is lying down in a horizontal position, such as in cases of injury. The head and neck must be supported during imaging, typically by a mattress, backboard, platform, or other support 150. Any supporting mattress or other support 150 may obstruct the intended path of the detector 104, or the radiation source 102, or both, such as when the radiation source 102 is in the end position 111 of its circular source orbit 108, as illustrated in FIG. 1B.

Some of the problems shown in FIG. 1B may be remedied using a multi-source system. Multi-source arrangements may minimize or eliminate the need for mechanisms that move or revolve the radiation source 102 and/or detector 104 and may simplify the mechanical requirements for scanning a head and neck to obtain volume image data.

The discussion above is merely provided for general background information and is not intended to be used as an aid in determining the scope of the claimed subject matter.

BRIEF DESCRIPTION OF THE INVENTION

A CBCT imaging system comprises a digital radiation detector and a radiation source. A detector transport moves the detector along at least a portion of a first curved path and a radiation source transport moves the radiation source along at least a portion of a second curved source path. The detector is configured to travel at least a portion of the first curved path, and the radiation source is configured to travel at least a portion of the second curved path. The detector is configured to obtain a plurality of 2D projection images over a range of scan angles for reconstructing a 3D volume image using the plurality 2D projection images. An advantage that may be realized in the practice of some disclosed embodiments of the head and neck imager is a CBCT imaging system that can obtain volume images of the head and neck while supporting the head and neck of the patient in a generally horizontal position.

In one embodiment, a CBCT imaging system comprises a digital radiation detector, a detector transport to move the detector along a curved path. The curved path extending at least partially around the head of a patient. A radiation source is moved along another curved path outside the first curved path and at least partially around the head of the patient. The detector is configured to travel at least a portion of the first curved path, and the radiation source is configured to travel at least a portion of the second curved path sufficient to allow a CBCT image capture by the detector. The detector is configured to obtain a plurality of 2D projection images over a range of image capture scan angles which are used to reconstruct a 3D volume image.

In another embodiment, a CBCT imaging system comprises a vertical height adjustable and tiltable gantry. A digital radiation detector and a radiation source are attached to the gantry. A detector transport attached to the gantry is configured to move the detector along a curved path at least partially around the head of a patient placed at a central axis of the curved path. A radiation source is moved along at least a portion of another curved path outside the detector's curved path. The radiation source and detector are configured to travel along their curved paths to allow sufficient radiation exposure of the head of the patient for capturing a plurality of 2D images and reconstructing a 3D volume therefrom.

In another embodiment, a CBCT imaging system comprises a support column, and a height adjustable and rotatable support arm attached to the support column. A digital radiation detector is attached to the support column and positioned such that the head of a patient may be placed above and proximate to a top planar surface of the detector. A radiation source moves along at least a portion of a curved source path extending at least partially around the head of the patient. The radiation source is aimed at the top planar surface of the detector while being rotated with respect to the support arm such that the radiation source remains aimed at the top planar surface of the detector when the support arm is rotated.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

The summary descriptions above are not meant to describe individual separate embodiments whose elements are not interchangeable. In fact, many of the elements described as related to a particular embodiment may be used together with, and possibly interchanged with, elements of other described embodiments. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

BRIEF DESCRIPTION OF THE DRAWINGS

So that the manner in which the features of the invention may be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIGS. 5A, 5B, 5C, and 5D are perspective views that show a CBCT imaging system having a rotating arm gantry configuration, with various aspects of gantry movement.

FIGS. 6A, 6B, and 6C show an embodiment for tomosynthesis with a detached detector.

FIG. 8A shows an alternate embodiment in which the platform pivots on the bed to allow positioning of the patient.

FIGS. 8B-8C are perspective views that shows how the pivoting platform positions the patient.

FIG. 10A shows a multi-source system with stationary detector.

FIG. 10B shows a multi-source system with an orbiting detector.

DETAILED DESCRIPTION OF THE INVENTION

Figure 1A:
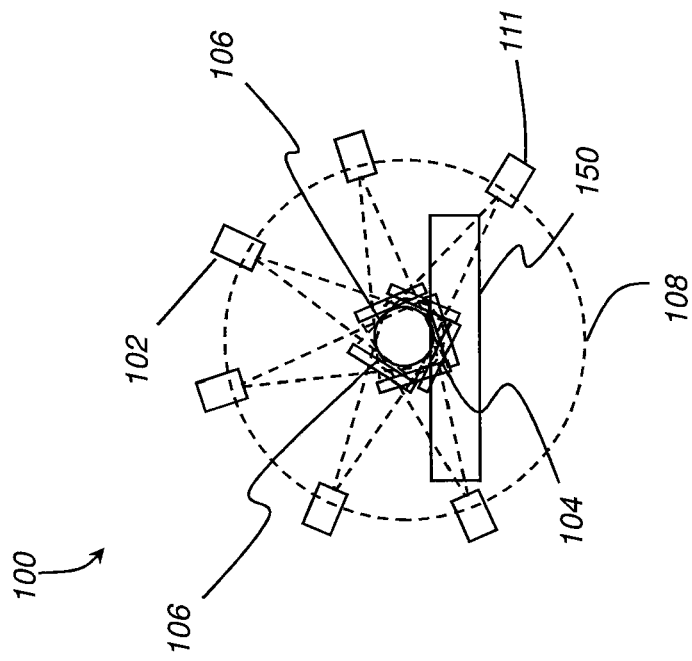
FIG. 1A is a schematic view that shows how CBCT projection images are obtained in conventional practice.
Figure 1B:
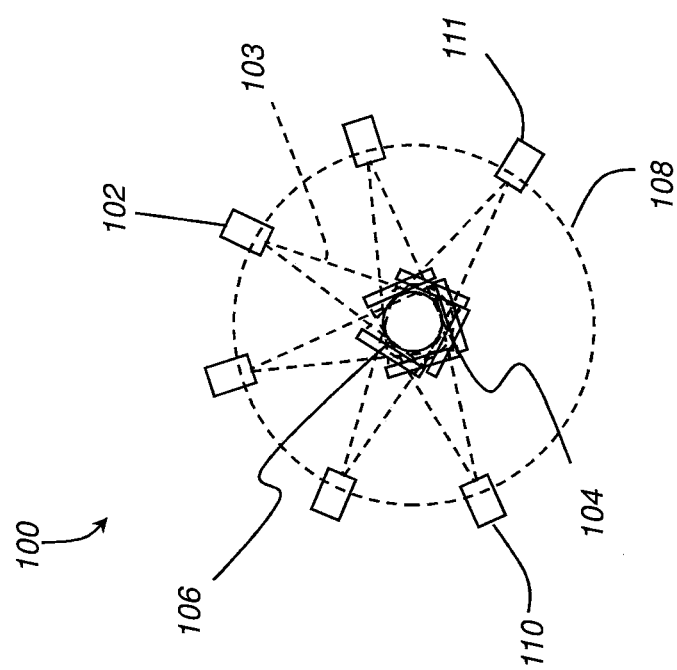
FIG. 1B is a schematic view that shows some of the inherent difficulties with head and neck imaging.
Figure 2:
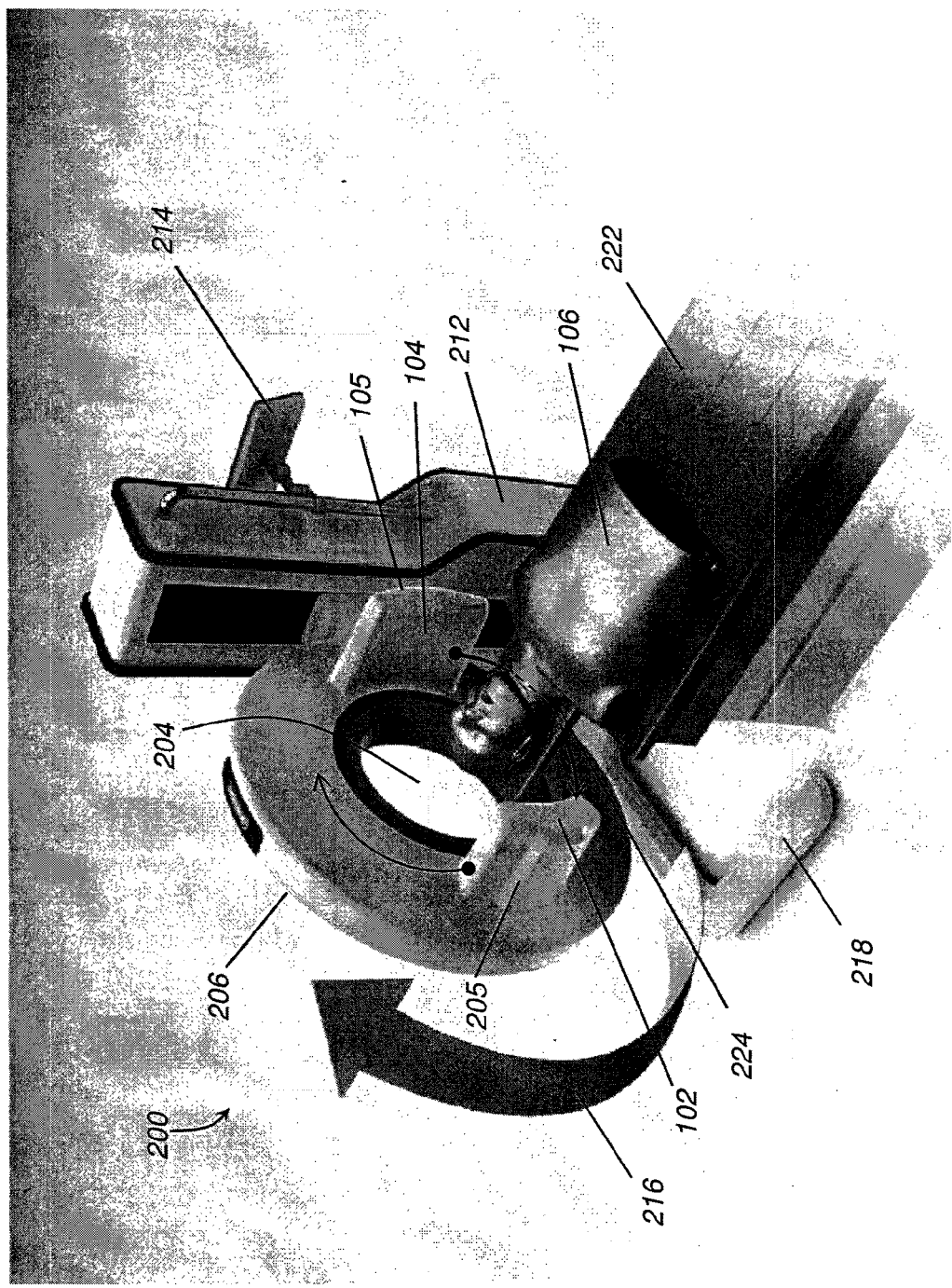
FIG. 2 is a perspective view of a CBCT imaging system having a gantry configuration with housings for detector and source.
Figure 3:
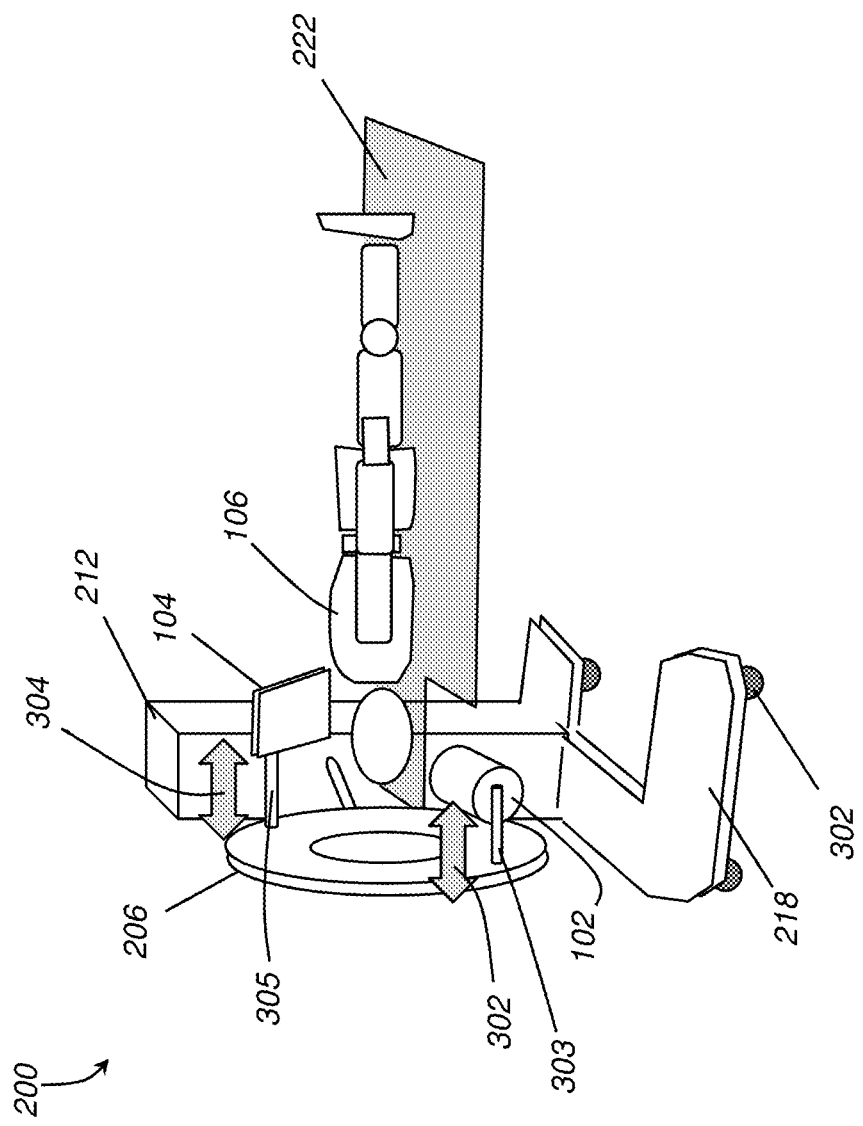
FIG. 3 is a perspective view of a CBCT imaging system having a gantry configuration with extendible housings for detector and source.
Figure 4C:
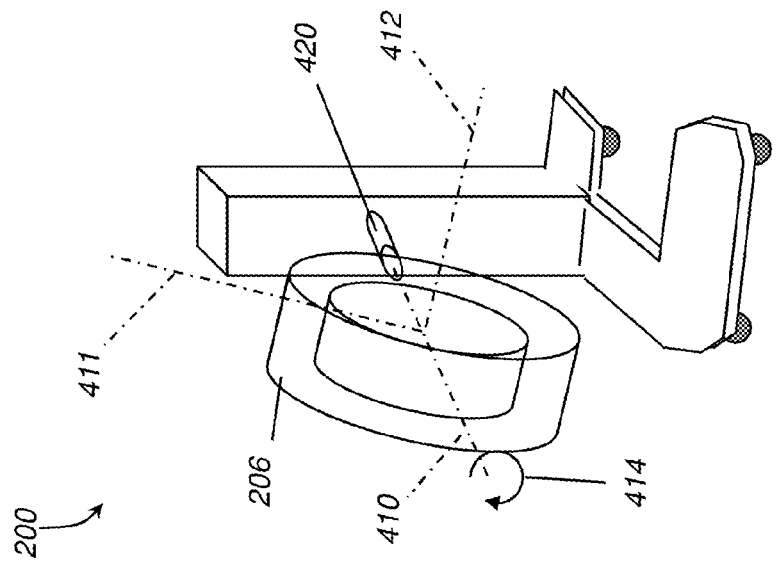
FIGS. 4A, 4B, and 4C are perspective views that show a CBCT imaging system having a gantry configuration, with various aspects of gantry movement.
Figure 4B:
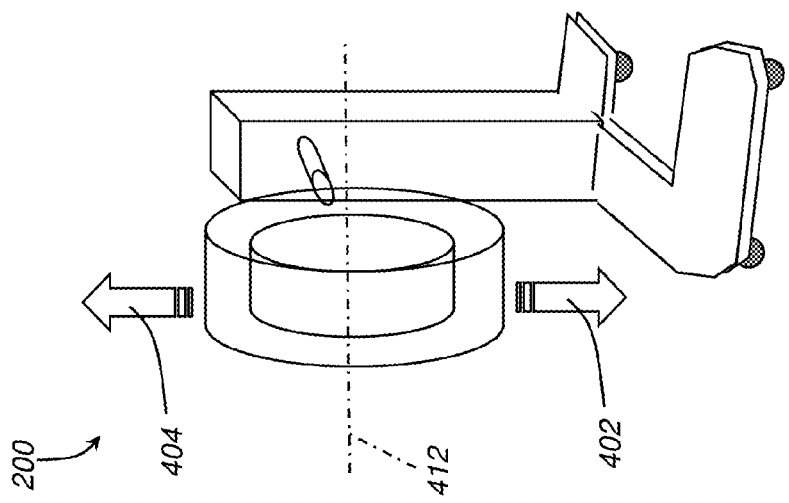
Figure 4A:
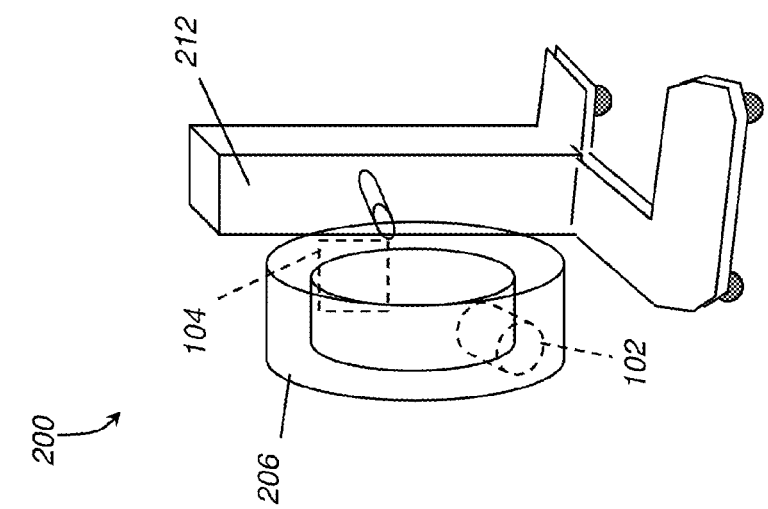

With reference to FIGS. 2, 3, and 4A-4C, a scanner gantry 206 mounts the radiation source 102 and DR detector 104 components for orbital movement about the head of the patient 106 in a direction indicated by the arrow 216 to achieve 180 degrees plus cone angle coverage of the head and neck. The scanner gantry 206 may be arranged in a number of ways. In one embodiment, shown schematically in FIGS. 2, 3, and 4A-4C, the radiation source 102 and detector 104 orbit the patient 106 within the outer circumference of the scanner gantry 206. The scanner gantry 206 may be vertically moved to adjust for the height of the bed or other platform 222 on which the patient 106 lies. The support column 212 supports the scanner gantry 206 and may include a motorized mechanism to move the scanner gantry 206 vertically 402, 404, as shown in FIG. 4B, as well as to tilt the scanner gantry 206. The support column 212 may also be attached to a base portion 218. The base portion 218 may also be fitted with wheels 302 for easing movement of the CBCT imaging system 200 across a floor. Such an assembly may be referred to herein as a wheeled base portion 218 for the CBCT imaging system 200. The scanner gantry 206 may be tilted about an axis 410 which is aligned with element 420, such as in the direction of the arrow 414, as shown in FIG. 4C, to tilt the axis of rotation 412 of the radiation source 102 and detector 104 with respect thereto. The axes 410, 412, may be said to be perpendicular. The axis 411 may be perpendicular to both axes 410, 412, and some amount of rotation about the axis 411 may also be provided. The radiation source 102 and detector 104 may be attached to extendible arms 303, 305 (FIG. 3), respectively, so that they may be extended outward or inward, as indicated by the arrows 302, 304, with respect to the scanner gantry 206, to an imaging position further or nearer to the scanner gantry 206.

Figure 5C:
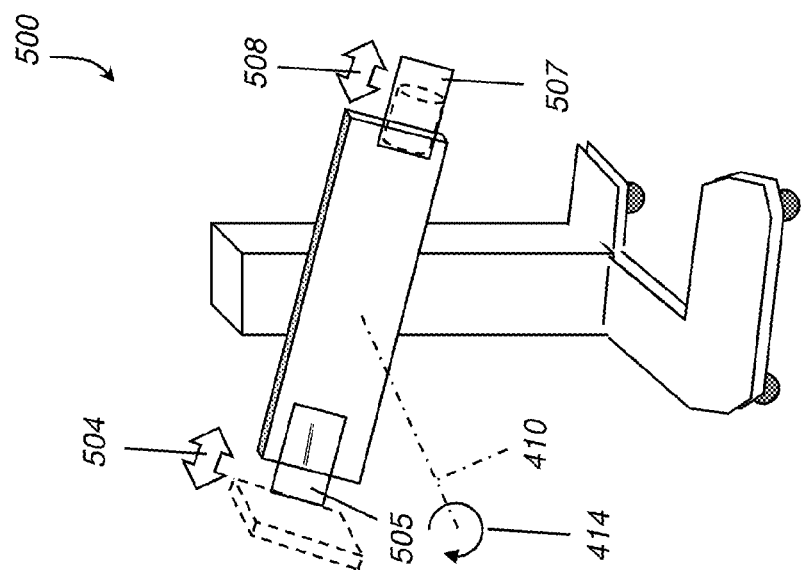
Figure 5B:
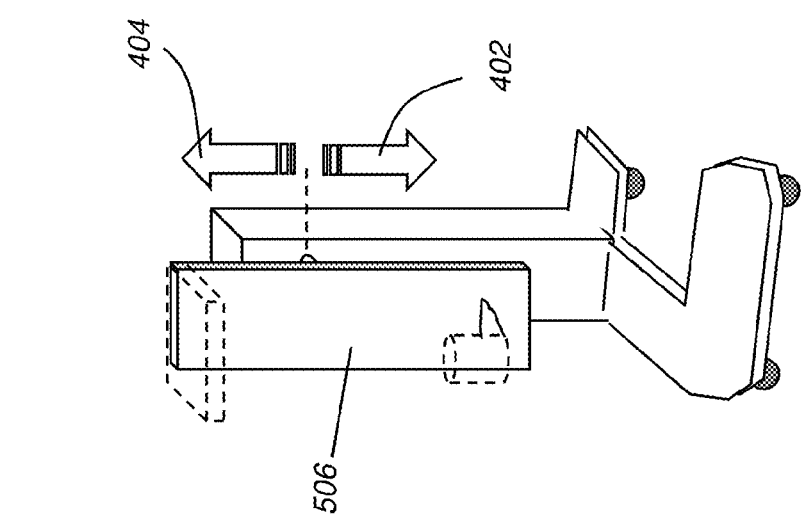
Figure 5A:
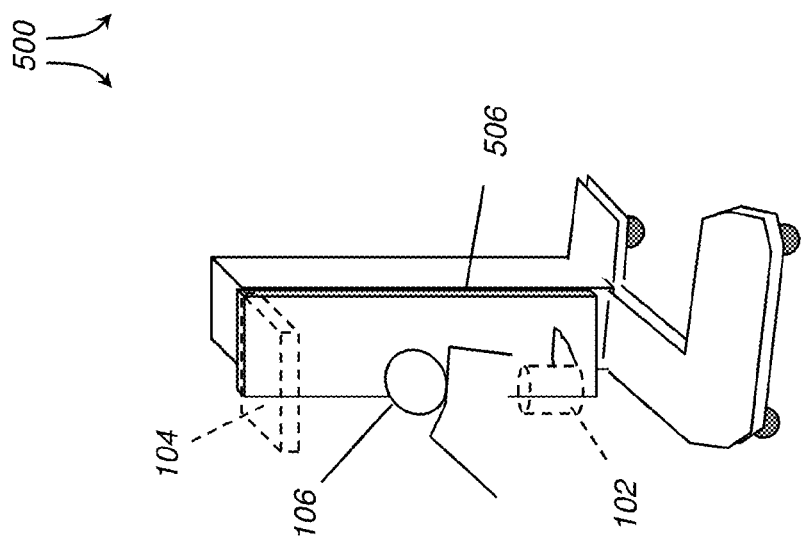

In another embodiment 500, shown schematically in FIGS. 5A-5D, a rotating arm 506 supports the radiation source 102 and detector 104. The rotating arm 506 may rotate about a central rotation axis 410 during a radiographic imaging scan using a rotating shaft 510, in the direction indicated by arrow 414, for example. FIG. 5D shows a side view. The rotating arm 506 may be vertically adjustable as indicated by the arrows 402, 404. In one embodiment (FIG. 5C), a variable source-to-image (source-to-detector) distance (SID) may be utilized by moving either the radiation source 102, detector 104, or both, toward or away from each other, as indicated by the arrows 504, 508, respectively, along support arms 505, 507, respectively. There are some limits with respect to the depth of this arrangement, since space may be needed for the patient's head.

In one embodiment 600, as illustrated in FIGS. 6A-6C, the radiation source 102 and detector 104 may be attached to a rotating arm 606 and positioned on separate, independently adjustable mounts, to allow independent movement. The detector 104 may be detached from the rotating arm 606, for example, and mounted to the support column 212, for example, beneath the patient 106. The radiation source 102 may be moved above the patient's head to desired exposure angles 602, 603, 604 by rotating it with respect to the rotating arm 606. This may be performed while rotating the rotating arm 606 using a rotating support shaft 510 in a direction as indicated by the arrow 614 to a desirable position as shown in the FIGS. 6A-C. This is similar to the movement pattern used in conventional mammography systems and similar to bedside tomosynthesis configurations. A radiation source 102 rotation of 90 degrees, for example, may be enabled. As in other embodiments described herein, the radiation source 102 may be extended inward or outward from the axis of rotation as shown in FIG. 5C, or may be extended nearer or further from the rotating arm 606 as shown in FIG. 3.

As disclosed herein, the scanner gantry 206 may serve as a housing or enclosure for at least a portion of the components that move and connect to the radiation source 102 and the detector 104. The scanner gantry 206 may be height adjustable and may rotate about the axis that corresponds to the head of the patient 106, e.g., a lengthwise body axis. Variable angular positioning of the scanner gantry 206 enables the patient 106 to be in a reclining or in a vertical position. A number of variable SID arrangements are possible, including a telescoping aim that moves detector 104 and/or radiation source 102 to different distances from the axis of rotation. Image processing adapts to different SID and angular ranges. The SID may be extended to accommodate patient shoulders, or bed dimensions. A collimator may be used to adjust the beam dimensions for each SID change.

Figure 7:
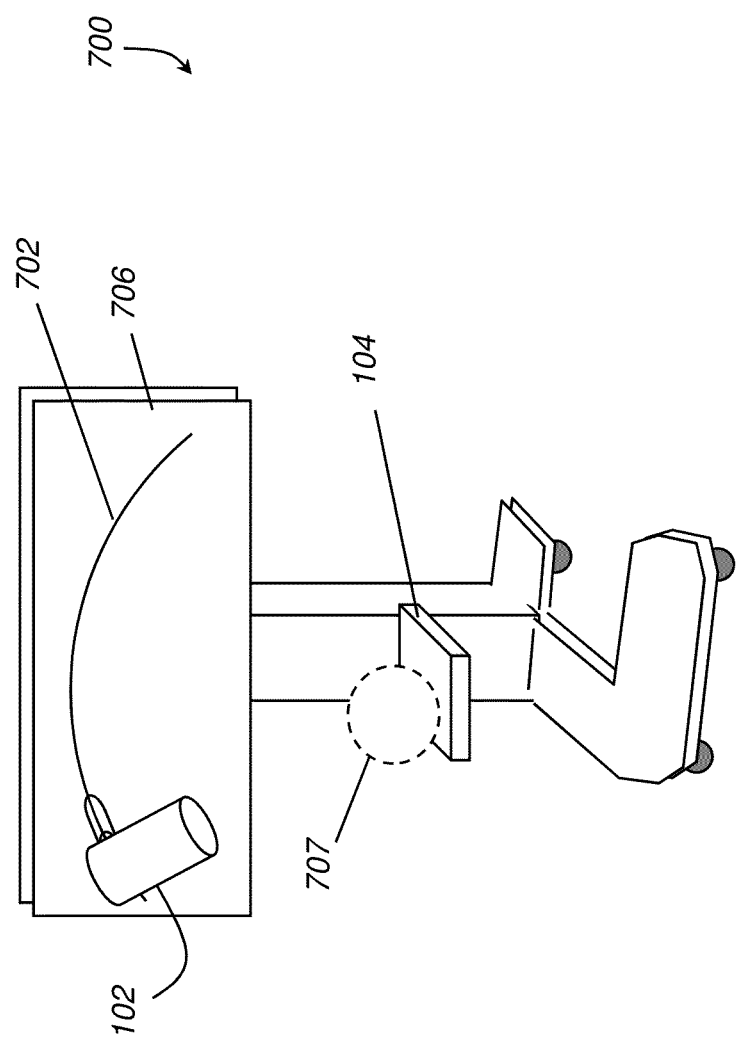
FIG. 7 shows an overhead gantry for a radiation source or detector.

The scanner gantry 206 itself may have telescoping sections. The scanner gantry 206 may support the radiation source 102 or detector 104 and provide movement from above the patient, so that the area around the patient's head is unobstructed. An arrangement of the radiation source 102 and detector 104 providing an unobstructed region around the patient's head is shown in FIG. 7 where a scanner gantry 706 is configured to provide a track 702 for movement of the radiation source 102 with respect to a detector 104. A patient's head may be positioned proximate the detector 104 in the area 707, for example, while the patient 106 is lying on a bed or other support that is rolled into close proximity to the CBCT imaging system 700 using an embodiment of the wheeled base portion 218 described herein.

With reference to FIGS. 8A-8C, a variable patient support platform 802 may be provided as part of the CBCT imaging system 800. The variable patient support platform 802 may be configured to fit within the bore 204 of the scanner gantry 206, or the variable patient support platform 802 may include a narrower portion 224 (FIG. 2) at one end of the platform 802 (222) beneath the head of the patient 106 that fits within the bore 204. The variable patient support platform 802 may be detachable from the main structure of the bed 804 or it may be movable, such as being rotatable or pivotable as illustrated in FIGS. 8A-8B and indicated by the arrow 806 in FIG. 8B, while still attached to the main structure of the bed 804, allowing the patient 106 to be lifted from the bed 804, or otherwise positioned appropriately so that the head of the patient 106 may be placed within the bore 204 for head imaging. FIG. 8A shows the variable patient support platform 802 fitted into the bore 204 of the CBCT imaging system 800. The variable patient support platform 802 may also be pulled forward from the bed 804 to fit into the bore 204 as indicated by the arrow 808 in FIG. 8B and demonstrated in FIG. 8A. These configurations of the CBCT imaging system 800 allow the imaging equipment 206, 218, to be moved alongside edges of the bed 804. Alignment sensors may be provided for proper alignment of the patient 106 and variable patient support platform 802 relative to the radiation source 102 and detector 104.

Figures 9A, 9B, 9C:
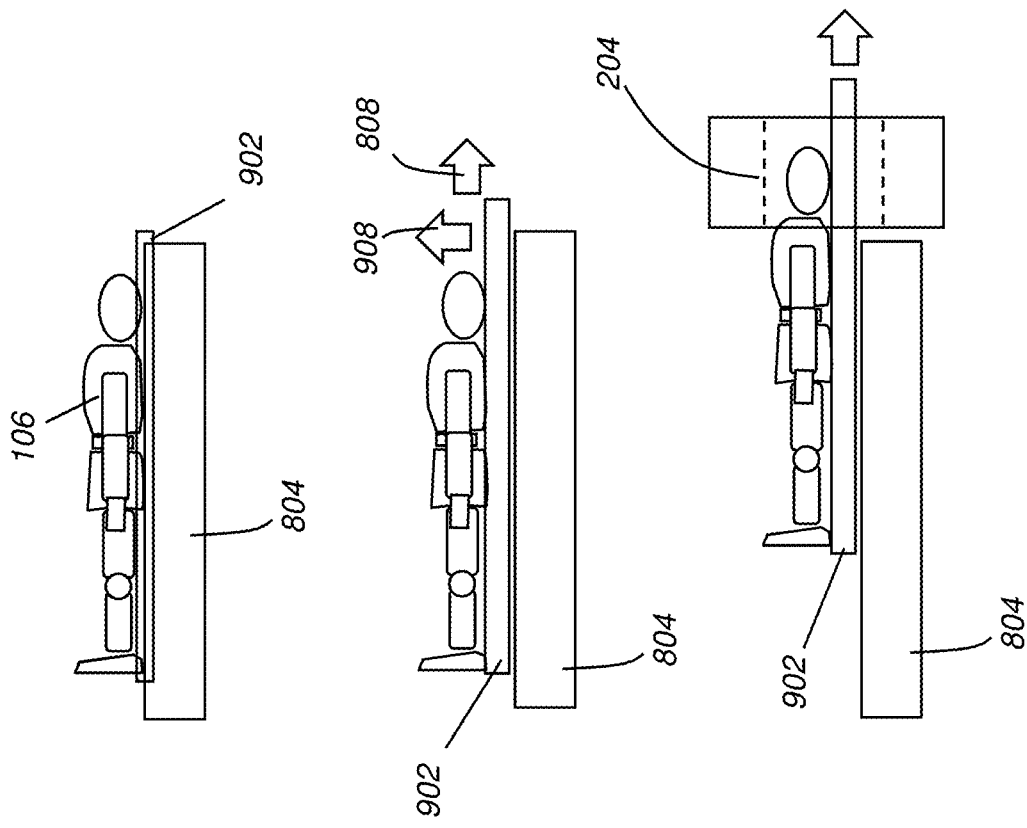
FIGS. 9A, 9B, and 9C show side views of an inflatable mat for patient support.

One or more elevation devices may be attached to the bed 804 and used for raising or lowering the patient 106 to the proper height for head imaging using the CBCT imaging system 800. FIGS. 9A-9C illustrate the use of an inflatable mat 902 to support the patient 106 and allow a height adjustment 908, and movement in the direction 808, for example, to align with the bore 204 height. A variety of cushioning and support devices, which may include foam and inflatable devices, for example, may be provided for stabilizing and positioning the patient anatomy such as in the direction 808 for the exam.

Referring again to FIG. 2, the scanner gantry 206 may be coupled to a support column 212 that provides controls for adjustable scanner gantry height, as described herein. A collapsible support column 212 may enable improved visibility and weight distribution for transport and use of the CBCT imaging system 200. A telescoping arrangement of the support column 212 may serve to provide gantry height adjustment. The radiation source 102 itself may be linear or curvilinear. Multiple radiation sources may be included, to be separately energized, such as sequentially, or energized as a group. For some gantry configurations, a radiation source housing 205 provides protection for the x-ray tube(s) or other radiation emitter(s) and related equipment. The radiation source housing 205 may provide a collimator for limiting the beam width and changing or scaling a beam aspect ratio.

The DR detector 104 may acquire images at a rate that is commensurate with energization and angular disposition of the radiation source 102. The detector 104 may transmit acquired data to a system processor over a wired or wireless transmission circuit. A detector housing 105 may provide protection for the digital detector 104 and related equipment, such as support electronics and battery. A number of different position encoders and sensors may be provided for the radiation source 102 and the detector 104, as well as for patient head position relative to radiation source and detector paths. A number of fiducial markings may also be provided to assist in alignment of the patient 106 or of system imaging components. Fiducials on the board, mattress, or bed help to assist alignment.

A computer or other type of logic processor may be disposed in the support column 212, and may communicate electronically with a display 214 attached thereto. The computer may interact with the image acquisition system components for setup, exposure control, scanning control including control of transport mechanisms, image data acquisition, and image processing and display. The processing logic may be distributed between multiple processors. Thus, for example, some of the image processing functions may be performed by a processor on the digital detector, prior to transmission of the acquired image data to the computer or other host processor. The display 214 may present an operator interface for use by a radiology technician, such as utilities for entry of operator commands. Operator interface components are in signal communication with the processor. The display may be a touchscreen display, for example. Input hardware may include a mouse, joystick, or control console, for example.

A laser-illuminated positioning system may be provided, for displaying guidelines and target markings for patient and equipment positioning. A camera with corresponding display screen, such as a remote display, may also serves to help visualize patient positioning. A radiation source transport apparatus orbits the radiation source 102 about the subject extremity to be imaged. The radiation source 102 generally orbits about a central point comprising a central rotation axis, so that the radius may have a fixed value for any CBCT imaging sequence. The radius of the orbit may be adjusted over a range to suit different imaging conditions. Thus, for example, the coupling arrangement by which the radiation source housing 205 is coupled to the radiation source transport apparatus allows a change to the orbital radius. This change in radius may be accomplished in a number of ways, such as by an adjustable offset from a threaded connector, for example.

For scan operation and coordinated movement, the radiation source transport apparatus is coupled to the detector transport apparatus. This allows the radiation source 102 to face the detector 104 at 180 degrees for imaging over the range of imaging angles, with the patient 106 between the radiation source 102 and the detector 104. One or more motors or other actuators may be used to move both the radiation source 102 and detector 104 at appropriate speed so that they are at the proper positional relationship with respect to the subject at each angle. Rotation of the radiation source 102 and detector 104 may also be manual.

According to an alternate embodiment, the radiation source transport apparatus may be de-coupled from the detector transport apparatus. Motion sensing may be provided, with position encoders on one or more of the axes. A variable orbital radius may be provided during the scan, according to an alternate embodiment of the present invention. This changes the SID to adjust for bed and shoulder obstruction. The starting and ending points of the scan sequence such are adjustable and may be displayed to the operator. The starting and/or ending point may be entered as an operator instruction. Alternately, the starting and ending points of the scan sequence may be set by the operator in manually positioning scanner components. A detector transport apparatus orbits the digital detector about the subject extremity to be imaged. As with the radiation source, the detector generally orbits about a central point, so that the radius has a fixed value for any CBCT imaging sequence.

The radius of the detector orbit may be adjusted over a range to suit different imaging conditions. Thus, for example, the coupling arrangement by which the detector housing 105 may be coupled to the detector transport apparatus allows a change to the orbital radius. This change in radius may be accomplished in a number of ways, such as by an adjustable offset from a threaded connector that protrudes through a slot in the detector transport mechanism, for example.

FIG. 10A shows a multi-source system 1000, with each radiation source 102 independently energizable. The multiple radiation sources 102 may be an array of individual radiation sources 102, a carbon nanotube array, or other array arrangement. In FIG. 10A, the detector 104a and sources 102 are stationary, wherein a partial ring of sources 102 is shown. FIG. 10B shows a multi-source system 1050 with an orbiting detector 104a. According to an alternate embodiment of the present invention, multiple stationary detectors 104 may be provided, with the arrangement around a curved path as shown in FIG. 10B. Each detector 104 may be paired with one or more radiation sources 102, so that energizing a particular radiation source 102 causes an image to be obtained by at least one detector 104. The radiation sources 102 may be arranged in two dimensions, so that radiation sources 102 are disposed in parallel about a central axis and also orthogonally arranged along the central axis. This pattern enables an axial or spiral scan pattern. Adjustable collimation may also be provided for multi source arrays. The scanning pattern may proceed in any direction, clockwise or counter-clockwise relative to the patient 106.

The wheeled base portion 218 allows the scanner to be positioned in tight spaces and around various life-support equipment for the patient 106. The wheeled base portion 218 may be battery powered and includes controls to regulate speed and other movement characteristics. A grid alignment utility may be provided. The wheeled base portion 218 may have a transport drive system comprising a drive handle responsive to operator control for movement and steering, wherein the drive handle may be adjustable for at least one of height and extension. Cabling for interconnection of detector and radiation source components as well as for signals and drive energy to control the detector and radiation source transport apparatus may be routed through the gantry. A cable guidance mechanism may be provided to route cables and tubing to the outside of the scan area.

Radiation shielding may be provided by the gantry and support column Additional shielding may be provided by coverings provided with the system. Lead apron(s) may be provided to cover portions of the imaging apparatus once positioned. Visual indication of the primary radiation coverage area may be provided, such as during scanner setup and prior to energizing the radiation source. This facilitates shielding placement, for example.

Detector and radiation source transport apparatus may be coupled together for imaging so that they both orbit the subject at the correct speed for image acquisition. Scanning may be executed by moving the scanner components in either direction, with either clockwise or counter-clockwise motion about the subject anatomy. In more general terms, the relative motion of the source and detector with respect to the subject may be in the clockwise or counter-clockwise direction.

The basic imaging sequence may be include the following steps:
1. Guide the scanner into position for imaging the head of the patient. This may require repositioning cables and working around life support equipment.
2. Position the patient to allow imaging by the scanner. This may require moving the patient so that the patient's head extends past the edge of the hospital bed. Patient movement can be performed in a number of ways, as described in more detail subsequently.

3. Provide any necessary shielding to reduce exposure of nearby persons.
4. Optionally test the scanner travel path in a "dry run" mode.
5. Execute the image exposure sequence.
6. Reposition the patient and remove the scanner A range of different scan patterns may be used, including patterns for CBCT imaging, for tomography imaging, and for other imaging modalities. Limited-angle scanning for tomography can be with radiation from the front or rear of the patient. The scan pattern may be helical. Where multiple sources are provided, the arrangement of the sources enables a range of different scan patterns, based on the spatial distribution of the sources.

A "dry run" mode is provided that enables the technician to check scanner motion prior to exposure. Manual movement of the scanner through the scan path is provided. Alternately, a slow motion scan movement sequence is provided. This helps to check that the scanner movement will not interfere with other equipment or be obstructed by the bed or other devices that support the patient. Dry run testing may be assisted by the system, so that manual movement of the scanner gantry may be supported by transport systems for the source and detector. An operator interface command for dry run testing places the system in a mode wherein hand pressure from the operator may be sensed and the scanning movement may be executed in slow motion as well as stopped at any point in the scan, such as when the operator wants to reposition a tube or wire, for example.

Imaging software includes volume image reconstruction software for CBCT and for tomosynthesis imaging. Imaging software includes algorithms for detection and suppression of wires, tubing, and other components that would otherwise cause imaging artifacts during volume reconstruction.

A support in the form of an inverted T may be provided for insertion under the patient and support that enables the patient to be urged forward so that the patient's head extends outside the edge of the mattress. A preformed bore insert may be provided to position the patient's head along the axis of rotation of the scanner. The insert may be foam or inflatable. Devices for head stabilization may be coupled with the scanner arrangement or provided separately. These devices include foam and inflatable cushions, for example. Variable SID adjustment allows for imaging with the patient on a variable size mattress or supporting platform. Angular adjustment of the gantry (FIG. 3C) allows the orbital plane to be adjusted for bed angle.

Operator instructions may be provided for options on positioning and constraining the patient. Based on the exam type, the operator instructions may show the options available for the exam. The operator may set energy levels (kVp) and make other settings and adjustments to exposure-related parameters. The angular range and resolution may be set and adjusted for variable starting and ending points of the scan sequence. The start and end angles may be displayed to the operator. The user interface allows exam initiation and termination. The operator interface screen displays results of 2-D projection images as they are captured, as well as the 3-D reconstructed image that may be generated. Various parameters related to the subject may be displayed and monitored during imaging, including heart rate, muscle tension, and other parameters. A touchscreen interface may be provided. Alternately, an optional keyboard and mouse may be used for command entry. Alerts and warning devices, visible and audible, may be provided to indicate readiness for and commencement of the scan sequence.

The detector and radiation source may be moved out of imaging position for guiding the patient's anatomy into the apparatus or exiting the imaging apparatus. Detents, fiducials, or other guides may be provided in order to obtain precise alignment. Laser guide lines may be provided to assist with patient or scanner positioning.

A calibration sequence may be provided for periodic recalibration of the detector. Consistent with at least one embodiment, exemplary methods/apparatus may use a computer program with stored instructions that perform on image data that may be accessed from an electronic memory. As can be appreciated by those skilled in the image processing arts, a computer program of an embodiment herein may be utilized by a suitable, general-purpose computer system, such as a personal computer or workstation. However, many other types of computer systems may be used to execute the computer program of described exemplary embodiments, including an arrangement of networked processors, for example.

The computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that may be connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, may refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that may be used as a temporary buffer or workspace by a microprocessor or other control logic processor device. Display data, for example, is typically stored in a temporary storage buffer that may be directly associated with a display device and may be periodically refreshed as needed in order to provide displayed data. This temporary storage buffer may also be considered to be a memory, as the term may be used in the present disclosure. Memory may be also used as the data workspace for executing and storing intermediate and final results of calculations and other processing. Computer-accessible memory may be volatile, non-volatile, or a hybrid combination of volatile and non-volatile types.

It will be understood that computer program products for exemplary embodiments herein may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

It should be noted that while the present description and examples are primarily directed to radiographic medical imaging of a human or other subject, embodiments of apparatus and methods of the present application may also be applied to other radiographic imaging applications. This includes applications such as non-destructive testing (NDT), for which radiographic images may be obtained and provided with different processing treatments in order to accentuate different features of the imaged subject.

Although sometimes described herein with respect to CBCT digital radiography systems, embodiments of the application are not intended to be so limited. For example, other DR imaging system such as dental DR imaging systems, mobile DR imaging systems or room-based DR imaging systems may utilize method and apparatus embodiments according to the application. As described herein, an exemplary flat panel DR detector/imager may be capable of both single shot (radiographic) and continuous (fluoroscopic) image acquisition. Further, a fan beam CT DR imaging system may be used.

Exemplary DR detectors may be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

While the invention has been illustrated with respect to one or more implementations, alterations and/or modifications may be made to the illustrated examples without departing from the spirit and scope of the appended claims. In addition, while a particular feature of the invention may have been disclosed with respect to only one of several implementations/embodiments, such feature may be combined with one or more other features of the other implementations/embodiments as may be desired and advantageous for any given or particular function. The term "at least one of" may be used to mean one or more of the listed items may be selected. The term "about" indicates that the value listed may be somewhat altered, as long as the alteration does not result in nonconformance of the process or structure to the illustrated embodiment. Finally, "exemplary" indicates the description may be used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An imaging system comprising:
    a digital radiation detector;
    a detector transport to move the digital radiation detector along at least a portion of a first curved path, the at least a portion of the first curved path extending at least partially around the head of a patient at a distance D1 from a central axis of the first curved path;
    a radiation source;
    a radiation transport to move the radiation source along at least a portion of a second curved source path outside the first curved path, the second curved source path extending at least partially around the head of the patient and having a distance D2 from the central axis greater than the distance D1;
    wherein the digital radiation detector is configured to travel at least a portion of the first curved path, the radiation source is configured to travel at least a portion of the second curved source path, the distance D2 is sufficiently long to allow sufficient radiation exposure of the head for a CBCT image capture by the digital radiation detector, and wherein the digital radiation detector is configured to obtain a plurality of 2D projection images over a range of image capture scan angles;
    a processor to reconstruct a 3D volume using more than one of the plurality of 2D projection images; and
    a substantially circular housing configured to contain the radiation source, the digital radiation detector, the radiation transport, and the detector transport, the substantially circular housing including an examination opening for placement of the head of the patient.

2. The imaging system of claim 1, wherein the radiation transport and the detector transport each includes a mechanism to independently move the radiation source and the digital radiation detector further from, or closer to, the central axis.

3. The imaging system of claim 2, wherein the radiation transport and the detector transport each include a mechanism to independently move the radiation source and the digital radiation detector parallel to the central axis.

4. The imaging system of claim 3, further comprising a patient transport comprising a base and a platform to support the patient in a horizontal prone position, the platform being rotatable in a horizontal plane with respect to the base of the patient transport.

5. The imaging system of claim 4, wherein the patient transport further comprises an extension mechanism to extend the platform in the horizontal plane in a direction away from the base of the patient transport.

6. The imaging system of claim 1, further comprising a wheeled transport cart configured to support the substantially circular housing, the wheeled transport cart for manually transporting the substantially circular housing over a floor.

7. An imaging system comprising:
    a vertical height adjustable and tiltable gantry;
    a digital radiation detector attached to the gantry;
    a detector transport attached to the gantry and configured to move the digital radiation detector along at least a portion of a first curved path, the first curved path extending at least partially around the head of a patient placed at a central axis of the first curved path, the digital radiation detector disposed at a distance D1 from the central axis;
    at least one radiation source;
    a radiation transport to move the at least one radiation source along at least a portion of a second curved source path outside the first curved path, the second curved source path extending at least partially around the head of the patient and having a distance D2 from the central axis greater than the distance D1,
    wherein the digital radiation detector is configured to travel along at least a portion of the first curved path, the at least one radiation source is configured to travel along at least a portion of the second curved source path, and wherein the distance D2 is sufficiently long to allow sufficient radiation exposure of the patient for capturing a plurality of 2D projection images of the head of the patient by the digital radiation detector;

a processor to reconstruct a 3D volume using more than one of the plurality of 2D projection images; and a substantially circular housing configured to contain the gantry, the substantially circular housing including an examination opening for placement of the head of the patient.

8. The imaging system of claim 7, wherein the radiation transport and the detector transport each includes a mechanism to independently move the at least one radiation source and the digital radiation detector further from, or closer to, the central axis.

9. The imaging system of claim 8, wherein the radiation transport and the detector transport each includes a mechanism to independently move the at least one radiation source and the digital radiation detector parallel to the central axis.

10. The imaging system of claim 9, further comprising a patient transport comprising a base and a platform to support the patient in a horizontal prone position, the platform being rotatable in a horizontal plane with respect to the base of the patient transport.

11. The imaging system of claim 10, wherein the patient transport further comprises an extension mechanism to extend the platform in the horizontal plane in a direction away from the base of the patient transport.

12. The imaging system of claim 7, further comprising a wheeled transport cart configured to support the substantially circular housing, the wheeled transport cart for manually transporting the substantially circular housing over a floor.

13. An imaging system comprising:

a support column;

a rotatable support arm attached to the support column, the rotatable support arm having a central rotation axis;

a digital radiation detector having a substantially planar shape attached to the support column, the digital radiation detector positioned such that the head of a patient may be place above and proximate to a top planar surface of the digital radiation detector;

and a radiation source attached to the rotatable support arm to move along at least a portion of a curved source path, the curved source path extending at least partially around the head of the patient and positioned further from the head of the patient than the digital radiation detector, the radiation source aimed at the top planar surface of the digital radiation detector, wherein the radiation source is configured to rotate with respect to the rotatable support arm such that the radiation source remains aimed at the top planar surface of the digital radiation detector when the rotatable support arm is rotated.

14. The imaging system of claim 13, wherein the radiation source is configured to move inward or outward from the central rotation axis.

15. The imaging system of claim 14, further comprising a patient transport for positioning the head of the patient proximate the top planar surface of the digital radiation detector, the patient transport comprising a base and a platform to support the patient in a horizontal prone position, the platform being rotatable in a horizontal plane with respect to the base of the patient transport.

16. The imaging system of claim 15, wherein the patient transport further comprises an extension mechanism to extend the platform in the horizontal plane in a direction away from the base of the patient transport.

17. The imaging system of claim 13, wherein the rotatable support arm is configured to capture images of the head of the patient at different angles without movement of the digital radiation detector.

18. The imaging system of claim 13, further comprising a wheeled transport cart attached to the support column and configured to support the support column, the wheeled transport cart for manually transporting the support column, the support arm, the digital radiation detector, and the radiation source over a floor.

19. The imaging system of claim 13, wherein the radiation source is configured to move nearer or further from the rotatable support arm.

* * * * *

UNITED STATES PATENT AND TRADEMARK OFFICE
CERTIFICATE OF CORRECTION

PATENT NO. : 9,808,211 B2
APPLICATION NO. : 14/537085
DATED : November 7, 2017
INVENTOR(S) : John Yorkston et al.

Page 1 of 1

It is certified that error appears in the above-identified patent and that said Letters Patent is hereby corrected as shown below:

Column 5, Line 44    Please replace "telescoping aim" with --telescoping arm--
Column 9, Line 6     Please replace "scanner" with --scanner.--

Signed and Sealed this
Twenty-fifth Day of September, 2018

Andrei Iancu
*Director of the United States Patent and Trademark Office*